United States Patent
Shuros et al.

(10) Patent No.: US 8,948,872 B2
(45) Date of Patent: Feb. 3, 2015

(54) STIMULATION PATCH WITH ACTIVE ADHESION

(71) Applicant: Cardiac Pacemakers, Inc., St. Paul, MN (US)

(72) Inventors: Allan C. Shuros, St. Paul, MN (US); Ismail Guler, Maple Grove, MN (US); Richard Charles Gunderson, Maple Grove, MN (US); Joel P. Grover, St. Paul, MN (US); Eric A. Mokelke, White Bear Lake, MN (US); Adam Grovender, Brooklyn Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/104,853

(22) Filed: Dec. 12, 2013

(65) Prior Publication Data
US 2014/0180357 A1    Jun. 26, 2014

Related U.S. Application Data

(60) Provisional application No. 61/745,428, filed on Dec. 21, 2012.

(51) Int. Cl.
*A61N 1/00* (2006.01)
*A61N 1/36* (2006.01)
*A61N 1/05* (2006.01)

(52) U.S. Cl.
CPC .......... *A61N 1/36117* (2013.01); *A61N 1/0558* (2013.01)
USPC .......................................................... 607/44

(58) Field of Classification Search
USPC .......................................................... 607/44
See application file for complete search history.

(56) References Cited

U.S. PATENT DOCUMENTS

| | | |
|---|---|---|
| 6,394,948 B1 | 5/2002 | Borst et al. |
| 7,497,824 B2 | 3/2009 | Taylor |

(Continued)

FOREIGN PATENT DOCUMENTS

| | | |
|---|---|---|
| WO | WO-2014099624 A1 | 6/2014 |
| WO | WO-2014099625 A1 | 6/2014 |

OTHER PUBLICATIONS

Thanh-Vinh, N., et al., "Micro suction cup array for wet/dry adhesion", 2011 IEEE 24th International Conference on Micro Electro Mechanical Systems (MEMS), (2011), 284-287.

(Continued)

*Primary Examiner* — Robert N Wieland
(74) *Attorney, Agent, or Firm* — Schwegman Lundberg & Woessner, P.A.

(57) ABSTRACT

System and methods for adhering a patch of stimulation electrode(s) to blood vessels to stimulate a target site on the blood vessel are described. In one embodiment, the system includes an adhesion patch and at least one electrode. The adhesion patch includes an active adhesion mechanism that may produce an adhesive force sufficiently strong to adhere the adhesion patch to the exterior of the blood vessel and to operationally position the at least one electrode for use in electrically stimulating a target site of the blood vessel. The adhesion patch may also include a release mechanism that is configured for a user to disengage the patch from the exterior of the blood vessel without significant trauma to the blood vessel. After being released, the adhesion patch may be re-adhered to a different target site of the blood vessel and stimulate the different target site.

20 Claims, 10 Drawing Sheets

(56) References Cited

U.S. PATENT DOCUMENTS

| | | | |
|---|---|---|---|
| 8,221,402 | B2 | 7/2012 | Francischelli et al. |
| 8,249,705 | B1 | 8/2012 | Kieval et al. |
| 2003/0109855 | A1 | 6/2003 | Solem et al. |
| 2005/0010263 | A1 | 1/2005 | Schauerte |
| 2005/0154418 | A1 | 7/2005 | Kieval et al. |
| 2006/0111626 | A1 | 5/2006 | Rossing et al. |
| 2008/0004673 | A1 | 1/2008 | Rossing et al. |
| 2008/0051864 | A1 | 2/2008 | Callas et al. |
| 2008/0103577 | A1 | 5/2008 | Gerber |
| 2009/0030478 | A1 | 1/2009 | Kieval et al. |
| 2009/0132002 | A1 | 5/2009 | Kieval |
| 2009/0299447 | A1 | 12/2009 | Jensen et al. |
| 2010/0023088 | A1 | 1/2010 | Stack et al. |
| 2011/0009929 | A1 | 1/2011 | Nuccitelli et al. |
| 2013/0310823 | A1 * | 11/2013 | Gelfand et al. .......... 606/33 |
| 2014/0180356 | A1 | 6/2014 | Shuros et al. |

OTHER PUBLICATIONS

"U.S. Appl. No. 14/104,786, Notice of Allowance mailed Jun. 11, 2014", 9 pgs.

"International Application Serial No. PCT/US2013/074754, International Search Report mailed Mar. 7, 2014".

"International Application Serial No. PCT/US2013/074754, Written Opinion mailed Mar. 7, 2014".

* cited by examiner

US 8,948,872 B2

STIMULATION PATCH WITH ACTIVE ADHESION

CLAIM OF PRIORITY

This application claims the benefit of priority under 35 U.S.C. §119(e) of U.S. Provisional Patent Application Ser. No. 61/745,428, filed on Dec. 21, 2012, which is herein incorporated by reference in its entirety.

TECHNICAL FIELD

This document relates generally to medical devices, and more particularly, to systems, devices and methods for delivering electrical stimulation.

BACKGROUND

Neural stimulation has been proposed as a therapy to treat high blood pressure. For example, it has been proposed that electrical stimulation can be used to reduce blood pressure when the electrical stimulation is directed at the baroreceptor regions to induce a baroreflex response. Baroreceptors play an important role in regulating blood pressure, and are located throughout the body, but primarily in the arch of the aorta and the carotid sinuses of the left and right internal carotid arteries. Through a negative feedback baroreflex system, the central nervous system can regulate the BP to maintain the blood pressure at a relatively stable level. For example, when the arterial pressure rises too high, the baroreceptors are activated and send nerve impulses to the brain which responds by controlling the pumping activity of the heart and blood vessel dilation to reduce the blood pressure.

The blood pressure response can fluctuate dramatically when different areas of the baroreceptor region are stimulated. For example, the blood pressure response at a first site within the baroreceptor region can be significantly different than the blood pressure response at a second site within the baroreceptor region that is within 1 mm of the first site. Thus, the implantation of a baromodulation device to stimulate a small baroreceptor region in the carotid sinus usually requires extensive mapping of the internal carotid arteries in order to find a desirable stimulation location along the carotid artery that provides an effective or an apparently most effective control of blood pressure. Currently, surgeons manually hold one or more electrode(s) at various locations along the carotid artery to map the baroreceptor region. This procedure takes significant time and effort due to the difficulty of manually positioning the electrode and maintaining steady and consistent blood pressure. Thus, the clinical procedure is often unable to access a full mapping area. Moreover, the manual operation may cause trauma, or introduce mechanical activation of the baroreceptors which may hinder the evaluation of the blood pressure responses to the electrical stimulation.

SUMMARY

Various embodiments described herein improve the process for mapping the baroreceptor region. For example, some embodiments adhere a patch of stimulation electrode(s) to an exterior of a blood vessel to stimulate a target site on the exterior of the blood vessel. By way of example, a system embodiment may comprise of an adhesion patch and at least one electrode. The adhesion patch may include an active adhesion mechanism configured to produce an adhesive force sufficiently strong to adhere the adhesion patch to the exterior of the blood vessel and to operationally position the at least one electrode for use in electrically stimulating a target site of the blood vessel. The adhesion patch may also be configured for a user to disengage the patch from the exterior of the blood vessel without significant trauma to the blood vessel. The adhesion patch may be configured with a size and a shape to partially wrap around the blood vessel and be in conformity with the blood vessel. The adhesion patch may also be configured with a suture area for use by the user to suture the adhesion patch in position on the exterior of the blood vessel.

A method embodiment for stimulating a target site of an exterior of a blood vessel may include adhering an adhesion patch to a target site of the exterior of the blood vessel, and stimulating the target site using the at least one electrode. An active adhesion mechanism on the adhesion patch may be used to cause the adhesion patch to adhere to the target site and to operationally position at least one electrode to the target site. The method may further comprise releasing the adhesion patch from the exterior of the blood vessel without significant trauma to the blood vessel, re-adhering the adhesion patch to a different target site of the exterior of the blood vessel, and stimulating the different target site using the at least one electrode.

A method embodiment for determining a desirable site of a carotid artery for baroreceptor stimulation may include adhering an adhesion patch to a first site of the exterior of the carotid artery, stimulating the first site using the at least one electrode with one or more stimulation vector configurations, sensing a physiological parameter during the stimulation of the first site, disengaging the adhesion patch from the first site using a release mechanism on the adhesion patch and re-adhering the adhesion patch to a second site of the exterior of the carotid artery, and determining a desirable stimulation site using the comparison of the sensed physiological parameter during stimulation at the first site and the sensed physiological parameter during stimulation at the second site.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Disclosed herein are systems, devices and methods for adhering a patch with stimulation electrode(s) to an exterior of a blood vessel. The adhesion patch may be configured to partially wrap around the blood vessel and adhere to the exterior of the blood vessel using an active adhesion mechanism to operationally position the at least one electrode for use in electrically stimulating a target site. For example, the target site may be a site within a baroreceptor region. The adhesion patch may also be configured for a user to disengage the adhesion patch from the exterior of the blood vessel using a release mechanism, and to re-adhere the adhesion patch to a different site on the exterior of the blood vessel. Thus, for example, the adhesion patch may be used to map multiple sites within a baroreceptor region such as a carotid sinus baroreceptor region. The stimulation electrode(s) may be temporarily adhered to various sites on an exterior of a carotid artery during the process of baromodulation mapping to select a desirable site on the exterior of a carotid artery based on a physiologic response to the stimulation. The adhesion patch may be used to position the stimulation electrode(s) for use to chronically stimulate the site in the baroreceptor region. The adhesion patch may also be used to adhere stimulation electrode(s) to other anatomical structures including arteries, veins, nerve bundles, tissues, and internal organs.

Figure 1A:
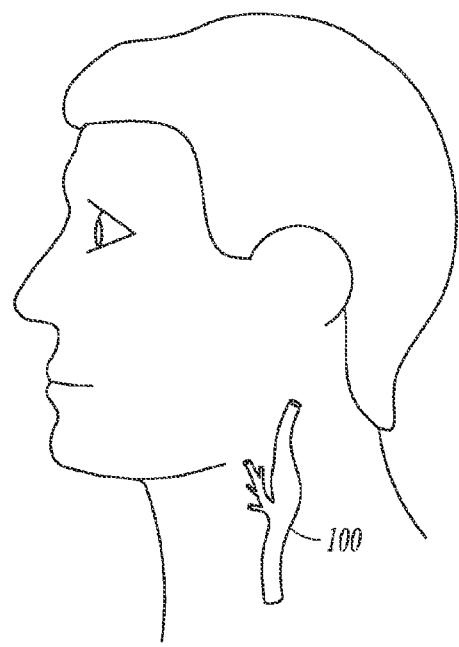
FIGS. 1A-B illustrate, by way of example, an embodiment of an adhesion patch adhered to the carotid artery.
Figure 1B:
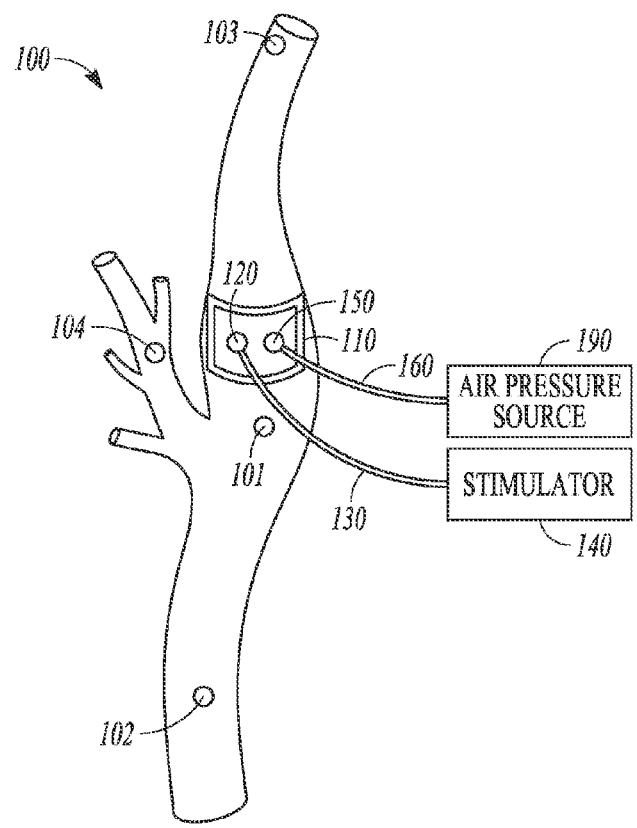

FIGS. 1A-B illustrate, by way of example, an embodiment of an adhesion patch adhered to a carotid artery. Illustrated anatomical structures in the cervical region include a segment of the carotid artery 100, a carotid sinus 101, a common carotid artery 102, an internal carotid artery 103, and an external carotid artery 104. An adhesion patch 110 is attached to a target site of an exterior of the carotid artery. The adhesion patch includes an adhesion mechanism (not shown) configured to produce an adhesive force sufficiently strong to adhere the adhesion patch 110 to the exterior of a blood vessel, such as the carotid sinus 101. In some embodiments, the adhesion patch also includes a release mechanism configured for a user to disengage the adhesion patch 110 from the exterior of the carotid artery without significant trauma to the carotid artery. After being released from the exterior of the carotid artery, the adhesion patch 110 can be re-adhered to a different site on the exterior of the carotid artery.

In the illustrated embodiment, the adhesion patch 110 is connected to a lead 130 via a coupling interface 120 located on or within the adhesion patch 110. The lead 130 is electrically connected to a stimulator 140 on one end and electrically connected to one or more electrodes (not shown) associated with the adhesion patch 110 on the other end. The stimulator 140 can be configured to provide desired electrical stimulation pulses to the one or more electrodes via the lead 130. The adhesion patch 110 is configured to operationally position the one or more electrodes for use in electrically stimulating the target site of the carotid artery. The one or more electrodes may interface with the target site of the exterior of the carotid artery. Some embodiments are designed to operate without a lead using wireless stimulation electrode(s). In some embodiments, the adhesion patch may be designed to adhere sensor(s) to a desired location. In some embodiments, the adhesion patch may be designed to adhere other therapy delivering mechanisms, such as drug patches, to a desired location.

In the illustrated embodiment, the adhesion patch 110 is also connected to an air pressure supply duct 160 via an air pressure receiving port 150 on the adhesion patch 110. The air pressure supply duct 160 connects an active adhesion mechanism on or within the adhesion patch 110 to an air pressure source 190. The air pressure source 190 may be configured to produce desired air pressure and feed the desired air pressure to the active adhesion mechanism, causing the adhesion patch to adhere to the target site of the exterior of the carotid artery.

Although FIGS. 1A-B illustrate the attachment of the adhesion patch 110 on the exterior of the carotid artery, the adhesion patch 110 can be used to adhere to other anatomical structures including interior and exterior of arteries and veins, nerve bundles, heart, skin, carotid body, stomach and intestines, bladder, soft tissues, neural tissue, gastric tissue, and other internal organs. The electrodes associated with the adhesion patch 110 may be used to stimulate various targets. Examples of the stimulation targets include baroreceptors, carotid body, nerve endings, nerve trunks, nerve bundles, myocardium, smooth muscle, skeletal muscle, gastric tissue, neural tissue, bladder, or other targets.

Figure 2:
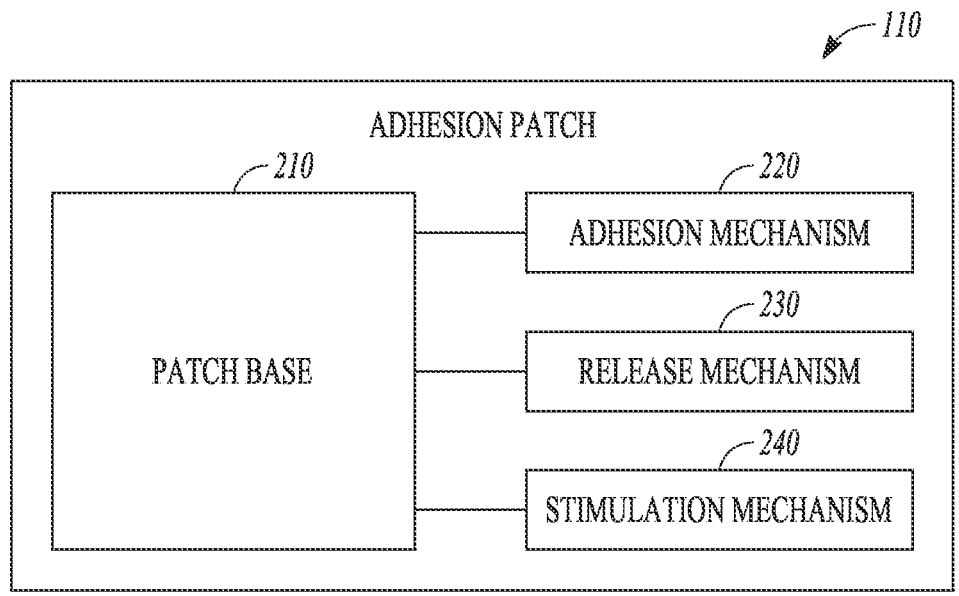
FIG. 2 illustrates, by way of example, an embodiment of an adhesion patch.

FIG. 2 illustrates, by way of example, an embodiment of the adhesion patch 110. The adhesion patch 110 may be configured to be used for adhering one or more electrodes associated with the adhesion patch to a target site of an exterior of a blood vessel, or other tissues or organs; and the electrodes can be used to stimulate the target site of the blood vessel and other tissues or organs. The adhesion patch 110 includes a patch base 210, an adhesion mechanism 220, an optional release mechanism 230, and a stimulation mechanism 240. The patch base 210 functions as a mechanical supportive structure for the adhesion patch 110. The patch base 210 may also function as a vehicle for the functional structures of the adhesion mechanism 220, the optional release mechanism 230, and the stimulation mechanism 240.

The patch base 210 may be made of biocompatible materials of desired rigidity, strength, and elasticity. In some embodiments, the patch base is made of one of materials including stainless steel, titanium alloy, polymers and other synthetic biocompatible materials. The patch base 210 may be customized to desired size and shape for use in contact and stimulation of the target site of a blood vessel, or other tissues or organs. The patch base 210 may be designed in a size and shape that allows the patch base 210 to partially wraps around the blood vessel. The patch base 210 may also be designed in a shape resembling a cuff that completely wraps around the blood vessel. The patch base may be designed as more than one inter-connected base pieces, each of which is configured to wrap around a certain portion of a blood vessel. The patch base 210 may also have a shape in conformity with the blood vessels. For example, the patch base 210 may have a concave shape with adjustable concavity to accommodate the circumferential shape of the blood vessel or other tissues or organs. The patch base 210 may be formed in a non-uniform shape to accommodate the shape of bifurcation of a portion of the blood vessel or tissues, such as bifurcation of carotid arteries.

Some embodiments of the patch base include a suture area configured for use by the user to suture the adhesion patch in a position on the exterior of the blood vessel. Thus, one a desired location is found, a surgeon may secure the patch in place with a suture. In some embodiments, the adhesion of the patch is sufficiently strong to remain in place without a suture at least until tissue growth secures the patch in place.

An embodiment of the adhesion mechanism 220 is configured to produce an adhesive force sufficiently strong to adhere the adhesion patch to an exterior of a blood vessel or other tissues or organs, and to operationally position one or more electrodes tier use in electrically stimulating a target site of the blood vessel. The adhesion mechanism 220 may be incorporated into the patch base 210 such that adhesion mechanism 220 is in direct contact with the target site of the blood vessel. The adhesion mechanism 220 may be incorporated into the patch base 210 with permanent fixation, and the adhesion mechanism 220 is engaged on at least one surface of the patch base 210. The adhesion mechanism 220 may include active adhesion mechanisms. For example, the adhesion is achieved by varying the air pressure in between the adhesion patch and the target site on the blood vessel or other tissues or organs. The adhesion mechanism 220 may also include passive adhesion mechanisms including suction cups. Details of active adhesion mechanism are discussed below, with reference to FIGS. 4-6.

When provided, the release mechanism 230 is configured for use to disengage the adhesion patch from the exterior of the blood vessel without significant trauma to the blood vessel. For example, a surgeon may use the release mechanism to disengage the adhesion patch. The release mechanism 230 may be incorporated into the patch base 210 such that a releasing force applied to the release mechanism 230 can cause disengagement of the patch base 210 from the target site of the blood vessel. The release mechanism 230 may include one or more air channels configured to pass positive air pressure to between the adhesion patch and the exterior of the blood vessel, to actively disengage the adhesion patch from the exterior of the blood vessel. In some embodiments, the release mechanism may include passive release mechanism provided on or within the adhesion patch. Details of the release mechanism are discussed below, with reference to FIGS. 4-9. When no release mechanism is provided, the patch may be released by a user to pull the adhesion patch with a force sufficient to overcome the adhesion force.

The stimulation mechanism 240 may include one or more electrodes on or within the patch base 210. The one or more electrodes are configured to provide electrical stimulation to the target site of a blood vessel. The one or more electrodes may be configured to be permanently fixed to the patch base 210. In some embodiments, the one or more electrodes are located on a side of the patch base 210 which incorporates the adhesion mechanism 220. The adhesion mechanism 220 causes the patch base 210 to be in tight contact with the target site of the blood vessel, thereby causing the stimulation mechanism 240 and the electrodes to be in tight contact with the target site of a blood vessel.

Figure 3:
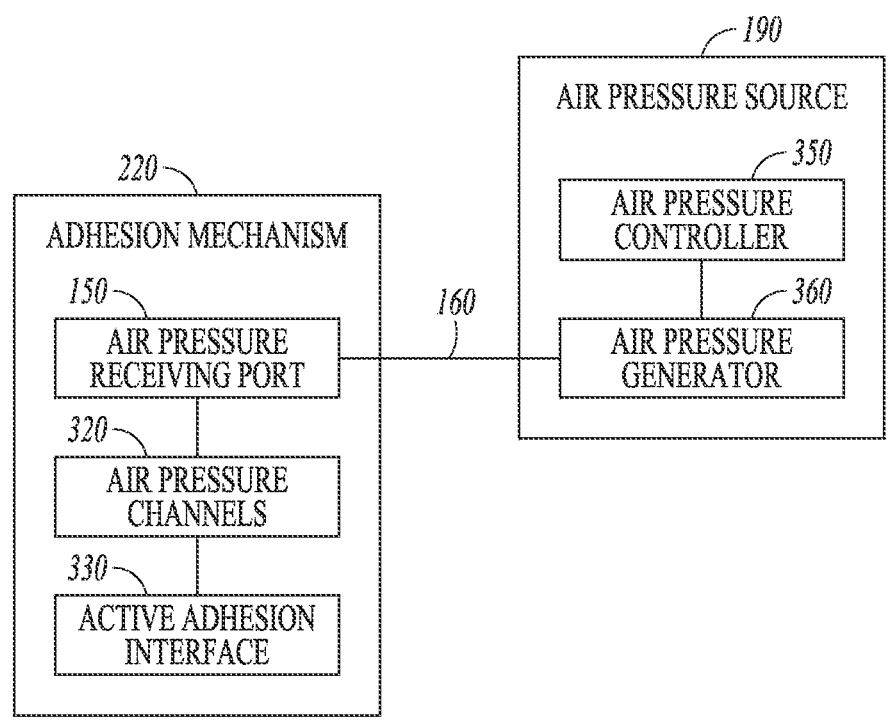
FIG. 3 illustrates, by way of example, an embodiment of an adhesion mechanism such as may be incorporated into the adhesion patch of FIG. 2.

FIG. 3 illustrates, by way of example, an embodiment of an adhesion mechanism 220 as may be incorporated into the adhesion patch of FIG. 2 and an air pressure source 190. The air pressure source 190 is configured to generate desired air pressure and provide the desired air pressure to the adhesion mechanism 220 through the air pressure supply duct 160. The illustrated air pressure source 190 includes an air pressure generator 360 and an air pressure controller 350. The air pressure generator 360 may be configured to generate the air pressure. Examples of the air pressure generator 360 may include an automatic pressure generator such as a vacuumed system used in a hospital, and a manual air pressure generator such as a syringe in which the positive and negative air pressures can be manually generated by a human operator. The air pressure controller 350 is configured to control the output of the desired air pressure from the air pressure generator 360, and deliver the desired air pressure to the adhesion mechanism 220. In some embodiments, the air pressure controller 350 is configured to generate desired level of negative air pressure (i.e., below the atmospheric pressure). The negative air pressure may be used to create an adhesive force between the adhesion patch and the exterior of the blood vessel that allows the adhesion patch to adhere to the target site on the blood vessel. In some embodiments, the air pressure controller 350 is configured to generate desired level of positive air pressure (i.e., above the atmospheric pressure). The positive air pressure may be used to create a release force between the adhesion patch and the exterior of the blood vessel that allows the adhesion patch to disengage from the target site on the blood vessel. In some embodiments, the air pressure controller 350 may be configured to be operated by a human operator to manually control the level of pressure to be released from the air pressure generator 360. In some other embodiments, the air pressure controller 350 may be configured to automatically adjust the level of air pressure in adaptation to the adhesive force or the releasing force created on the interface between the adhesion mechanism and the target site of the blood vessel, or in adaption to a physiologic parameter sensed from the patient. The air pressure controller 350 may also operate according to a pre-determined protocol to gradually increase the level of positive pressure or negative pressure from a first value to a second value within a specified time period, so that a desired adhesion or release effect can be achieved without significant trauma to the target tissue.

The illustrated adhesion mechanism 220 includes an air pressure receiving port 150, one or more air pressure channels 320, and an active adhesion interface 330. The air pressure receiving port 150 may be configured to receive the desired air pressure from the air pressure source 190 through the air pressure supply duct 160. In some embodiments, the air pressure receiving port 150 may include an adaptor to allow airtight connection to the air pressure supply duct 160. The air pressure receiving port 150 may also include an over-pressure protection mechanism that automatically resets the pressure to the atmospheric pressure if the pressure provided to the adhesion patch is above a pressure threshold. This would prevent potential trauma to the blood vessel or tissue in contact with the adhesion patch due to excessive air pressure. In some embodiments, the over-pressure protection mechanism may be designed to shut off the air pressure provided by the air pressure source 190 or automatically disrupt the airtight connection.

The one or more air pressure channels 320 may be configured to be coupled to the air pressure receiving port 150, receive the desired air pressure, and pass the desired air pressure to between the adhesion patch and the exterior of the blood vessel. The air channels 320 may have openings on the active adhesion interface 330 on the adhesion patch and directly contact the target tissue. Details of the air pressure channels are discussed below, with reference to FIGS. 4-9.

Figure 4A:
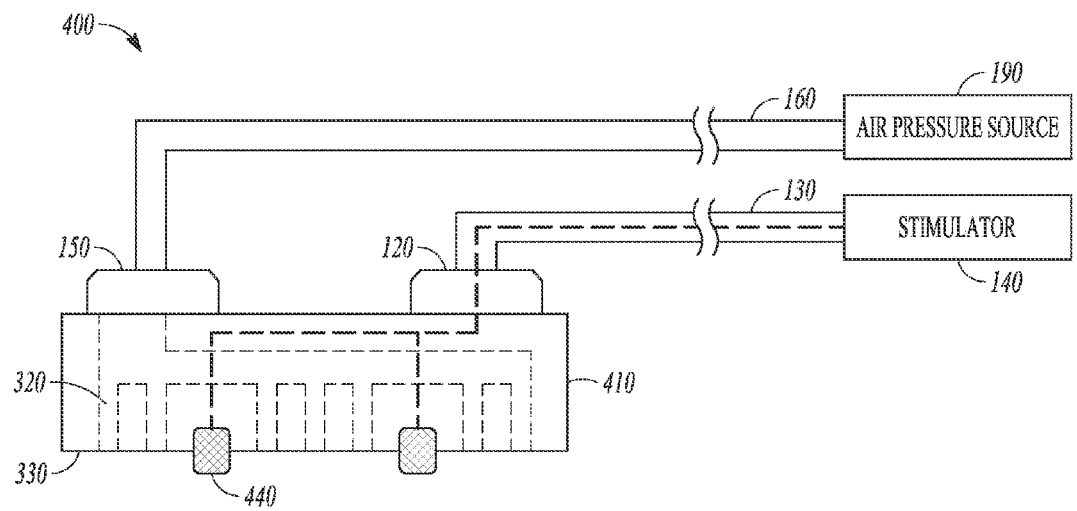
FIGS. 4A-B illustrate, by way of example, an embodiment of the adhesion patch with one or more air channels.
Figure 4B:
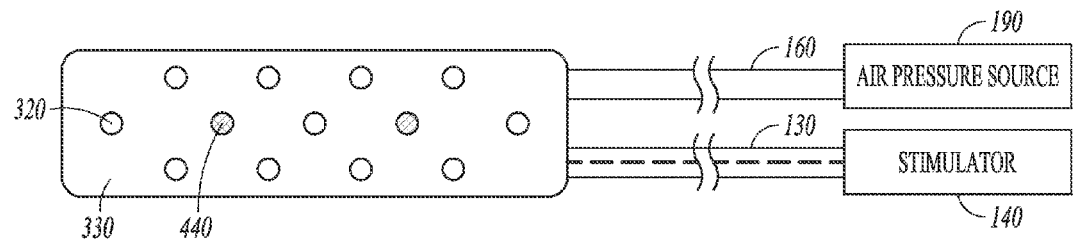

FIGS. 4A-B illustrate, by way of example, an embodiment of the adhesion patch with one or more air channels. The adhesion patch 400 is a specific embodiment of the adhesion patch 110 used for adhering the stimulation electrodes to the exterior of blood vessels or other tissues or organs for target site electrical stimulation. The adhesion patch 400 includes a patch base 410, one or more air channels 320, an active adhesion interface 330, one or more stimulation electrodes 440 (two shown in FIGS. 4A-B), a stimulation interface 120, and an air pressure receiving port 150. The patch base 410 is a specific embodiment of the patch base 210. The patch base 410 provides a supporting structure for suction mechanisms, the electrodes, and the stimulation interface and the air pressure port. The patch base 410 may be made of non-conductive compliable biocompatible materials. Such material allows the patch base 410 to be formed into various shapes and curvatures that are in conformity with the geometry of the target site on the exterior surface of the blood vessel. The patch base 410 may start out in a planer state, and is configured to be convexly shaped into curved surfaces such as the surfaces of veins, arteries, and nerve bundles. In some embodiments, the patch base 410 is configured to be shaped in conformity with the geometry of carotid bifurcation at 101. The patch base 410 may be made with a shape memory material, which allows the patch base to return to a planar shape after being removed from the target area on the blood vessel or tissues.

The adhesion patch may be configured to be in connection with a lead 130 via an interface 120 on or within the adhesion patch. The lead 130 is electrically coupled to a stimulator 140, which generates electrical stimulation pulses and conducts the stimulation pulses through the lead 130 to the stimulation electrodes 440 on the adhesion patch. As illustrated in FIGS. 4A-B, the adhesion patch may include an air pressure receiving port 150 which is connected to the air pressure source 190 via air pressure supply duct 160.

The active adhesion interface 330 may be configured to be in contact with the exterior of the blood vessel or other target tissue. Various number and distribution patterns of the air channels on the adhesion patch are contemplated. In some embodiments, as illustrated in FIGS. 4A-B, the openings of air channel 320 and the electrodes 440 are all located on the active adhesion interface 330 of the adhesion patch. The one or more air pressure channels 320 are configured to be coupled to the air pressure receiving port 150 to receive the desired air pressure, and pass the desired air pressure to between the adhesion patch and the exterior of the blood vessel. In some embodiments, the one or more air channels 320 are configured to pass negative air pressure to evacuate air from between the active adhesion interface 330 and the exterior of the blood vessel to adhere the adhesion patch to the exterior of the blood vessel. The one or more air channels 320 may also function as release mechanism. In some embodiments, the one or more air channels 320 are configured to pass positive air pressure to between the adhesion patch and the exterior of the blood vessel to disengage the adhesion patch from the exterior of the blood vessel.

As illustrated in FIGS. 4A-B, a planer array of air channel openings may be designed such that each stimulation electrode 440 is surrounded by a plurality of air channel openings to enhance tissue stabilization during suction and to allow reliable electrode-tissue contact. The air channel openings may be designed to have sizes that allow adequate suction force onto the surface of the target tissue, and at the same time avoid pulling the target tissue into the openings or causing significant tissue stretching. In one embodiment, the air channel openings may have a diameter of approximately 0.1-2 millimeters. In some embodiments, the stimulation electrodes 440 can protrude from the active adhesion interface 330 of the adhesion patch (as shown in FIGS. 4A-B). Such a design would ensure close electrode-tissue contact when the suction cups adhere to the tissue. In other embodiments, the electrodes 440 may recess to the same level as the active adhesion interface 330.

Figure 5:
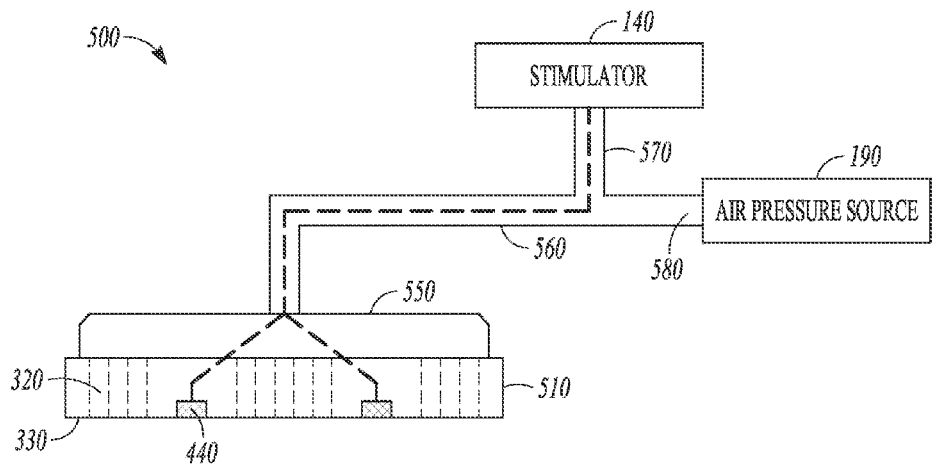
FIG. 5 illustrates, by way of example, an embodiment of the adhesion patch with one or more air channels.

FIG. 5 illustrates, by way of example, an embodiment of the adhesion patch 500 with one or more air channels. The illustrated adhesion patch 500 includes an integrated stimulation-air pressure port 550. The integrated port 550 functions both as an interface for the electrical connection between the stimulation electrodes 440 and the stimulator 140, and as an interface for the air pressure supply between the air channels 320 on the adhesion patch and the air pressure source 190. The integrated stimulation-air pressure port 550 connects to the stimulator 140 and the air pressure source 190 through an integrated stimulation-air pressure catheter 560. The integrated catheter 560 may include a stimulation port 570 and an air-pressure port 580 along the catheter. In some embodiments, the stimulation port 570 or the air-pressure port 580 may be located on a proximal end of the catheter. The stimulation port 570 is configured to be electrically coupled to the stimulator 140, and the air-pressure port 580 is configured to be mechanically coupled to the air pressure source 190. In some embodiments, the integrated catheter 560 may include a concealed air pressure duct encompassing insulated electrical wires electrically connecting the stimulation electrodes 440 and the stimulator 140. In other embodiments, the integrated catheter 560 may include a lumen configured to pass airflow between the air pressure source 190 and the air channels on the adhesion patch. The integrated catheter is configured to be electrically coupled to the integrated port and conduct the stimulation pulses from the stimulator 140 to the stimulation electrodes 440 on the adhesion patch. Other embodiments of configurations that combine the electrical connections and the air-pressure connections into one entity are also contemplated, and should be considered as within the scope of the integrated stimulation-air pressure port 550.

Figure 6A:
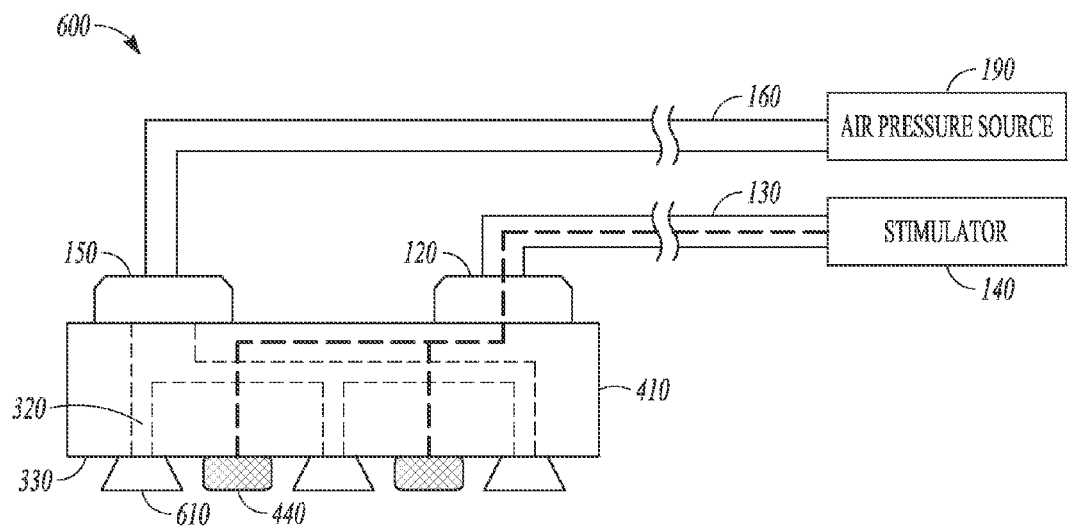
FIGS. 6A-C illustrate, by way of example, an embodiment of the adhesion patch with suction cups coupled with air channels.
Figure 6B:
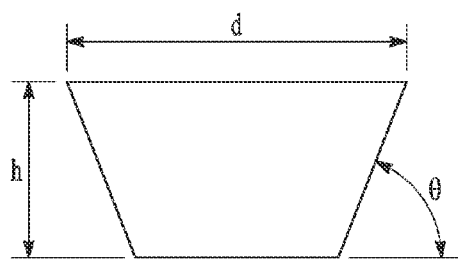
Figure 6C:
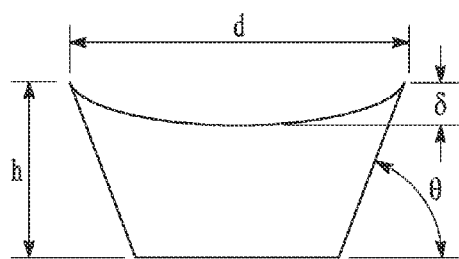

FIGS. 6A-C illustrate, by way of example, an embodiment of the adhesion patch with suction cups coupled to air channels. The adhesion patch 600 is a specific embodiment of the adhesion patch 110 used for adhering the stimulation electrodes to the exterior of blood vessels or other tissues or organs for target site electrical stimulation. As illustrated in FIG. 6A, the adhesion patch 600 includes a patch base 410, one or more suction cups 610, and one or more stimulation electrodes 440 (two shown in FIG. 6a). In some embodiments, the suction cups 601 may have different dimensions and can be irregularly distributed. FIG. 6B illustrates, by way of example, an embodiment of dimensional parameters of a suction cup with flat surface, and FIG. 6C illustrates, by way of example, an embodiment of the dimensional parameters of suction cup with concave surface, where the degree of concavity is determined by pitch δ. The shape and dimension of the suction cup are selected to obtain desired adhesion and atraumatic performance. Various sizes of the suction cup 601, defined by d, are contemplated for the present application of adhesion on the blood vessels. In some embodiments, the suction cups 401 are macroscopic cups. For example, the cup surface diameter d is in the range of 0.5-5 mm. In some embodiments, the suction cups 401 are microscopic cups. For example, the cup surface diameter d is in the range of 100-500 µm. The suction cups may be made of biocompatible materials including silicone, polymer, and other synthetic materials that are soft enough to promote atraumatic adhesion between the adhesion patch and the target site of the blood vessel or other tissues. In some embodiments, a biocompatible conductive fluid or wet gel may be included within and between suction cups. The gel or fluid provides purely viscous or visco-elastic properties so as to improve the adhesion between the suction cups and the tissue.

The one or more suction cups 610 are configured to be connected to the one or more air channels 320 and receive desired air pressure from the air pressure source 190. The suction cups 610 and the one or more air channels 320 may function as adhesion mechanisms that actively adhere the adhesion patch to the exterior of the blood vessel. In some embodiments, the air pressure source 190 generates and passes negative air pressure to the air channels 320 and then to suctions cups 610. The negative air pressure evacuates air from between the suction cups 610 and the exterior of the blood vessel, causing the suction cups 610, and hence the adhesion patch, to adhere to the exterior of the blood vessel and maintain the adhesion. In some embodiments, the suction cups 610 and the one or more air channels 320 may also function as release mechanisms that actively disengage the adhesion patch from the exterior of the blood vessel. In some embodiments, the air pressure source 190 generates and passes positive air pressure to the air channels 320 and then to suctions cups 610. The positive air pressure between the suction cups 610 and the exterior of the blood vessel would cause the suction cups 610 and hence the adhesion patch to disengage from the exterior of the blood vessel.

Various number and distribution patterns of the suction cups may be provided on the adhesion patch. In some embodiments, the suction cups and the stimulation electrodes 440 are all located on the adhesion interface 330. The suction cups form a planer array such that each stimulation electrode is surrounded by a plurality of suction cups. This may enhance tissue stabilization during suction and ensure reliable electrode-tissue contact. In some embodiments, the suction cups 610, the electrodes 440, or both the suction cups 610 and the electrodes 440 may protrude from the active adhesion interface 330 (as illustrated in FIG. 6A). In other embodiments, the suction cups 610, the electrodes 440, or both the suction cups 610 and the electrodes 440 may recess to the same level as the active adhesion interface 330. In a specific embodiment, the suction cups 610 have openings at the same level as active adhesion interface 330, while the electrodes 440 protrude from the active adhesion interface 330. Such a design would allow tight electrode-tissue contact when the suction cups adhere to the tissue.

Figure 7A:
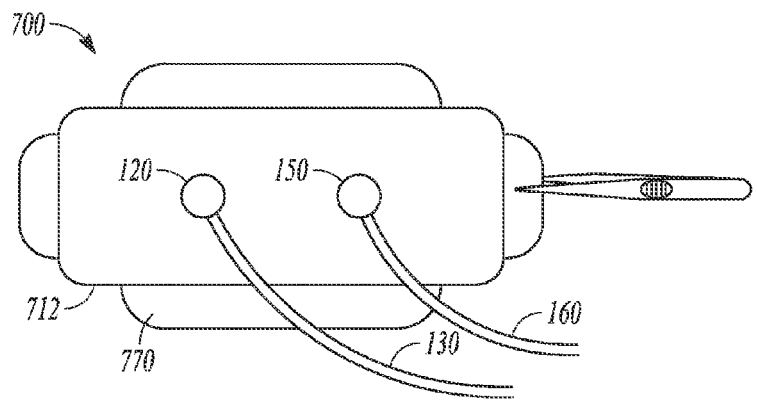
FIGS. 7A-C illustrate, by way of example, an embodiment of the adhesion patch with a release tab, and the application of the adhesion patch to an exterior of a blood vessel.
Figure 7B:
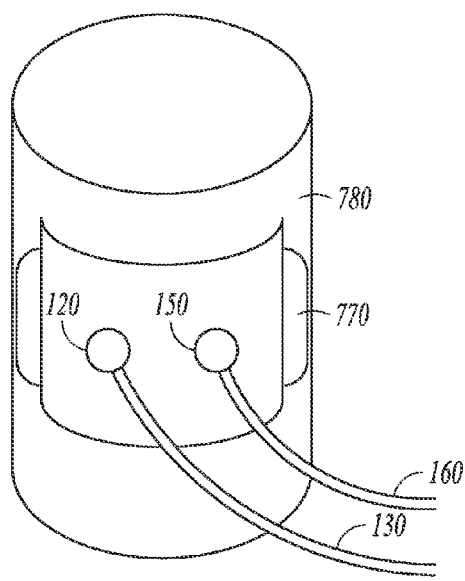
Figure 7C:
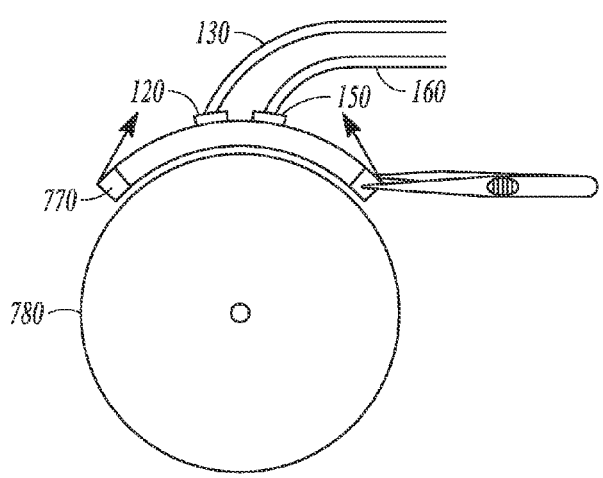

FIGS. 7A-C illustrate, by way of example, an embodiment of the adhesion patch 700 with a release tab 770, and the application of the adhesion patch 700 to the exterior of a blood vessel 780. The illustrated release tab 770 may be used together with an active release mechanism (such as the air pressure channels within the adhesion patch as illustrated in FIGS. 4-6) to disengage the adhesion patch from the exterior of the blood vessel.

The adhesion patch 700 includes one or more peripheral margin 712 and a release tab 770 along at least a portion of the peripheral margin 712. The release tab 770 allows for use by the user to peel off the adhesion patch 700 from the exterior of the blood vessel 780 using a surgical tool such as forceps. The release tab 770 does not include adhesion mechanisms and is not configured to adhere to the exterior of the blood vessel 780, such that it can be seized by the user using the surgical tool, and the adhesion patch 700 can be peeled off from the exterior of the blood vessel 780 (e.g., along one of the directions shown by arrows in FIG. 7C). In some embodiments, the release tab 770 may also be used as the suture site for permanently suturing the adhesion patch 700 to the target site on the blood vessel or other tissues.

Figure 8:
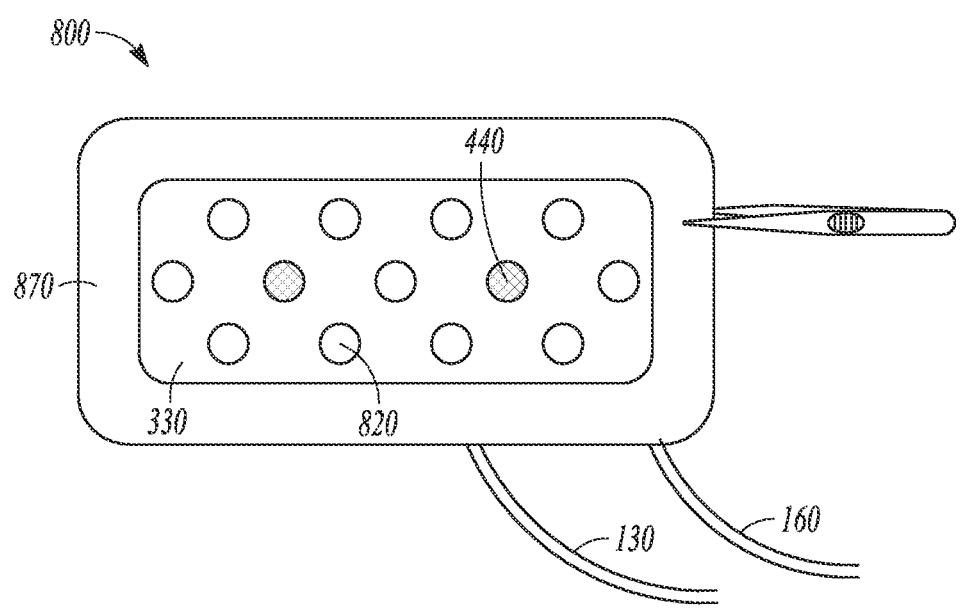
FIG. 8 illustrates, by way of example, an embodiment of the adhesion patch with a non-adhesive boundary region.

FIG. 8 illustrates, by way of example, embodiments of the adhesion patch 800 with a release mechanism configured for use by the user to disengage the adhesion patches from the exterior of the blood vessel. The adhesion patch 800 is a specific embodiment of the adhesion patch 110. The adhesion patch 800 may be used together with the active release mechanism that disengages the adhesion patch from the exterior of the blood vessel by passing positive air pressure to between the adhesion patch and the exterior of the blood vessel, as illustrated in FIGS. 4-6.

The adhesion patch 800 may include one or more air pressure channel openings 820, one or more stimulation electrodes 440 (two shown in FIG. 8) on a tissue contacting surface 330, and a portion of boundary region 870. The air pressure channel openings 820 may be the openings of the air pressure channels 320 as illustrated in FIGS. 4-5, or the opening of suction cup 610 as illustrated in 6A. The boundary region 870 does not include air channels, suction cups, or other adhesion mechanisms. The boundary region 870 is configured not to adhere to the exterior of the blood vessel 780 such that it can be seized by the user using a surgical tool such as forceps, and the adhesion patch 800 may be peeled off from the exterior of the blood vessel. In some embodiments, the boundary region 870 may also be used as the suture site for permanently suturing the adhesion patch 800 to the target site on the blood vessel or other tissues.

Figure 9A:
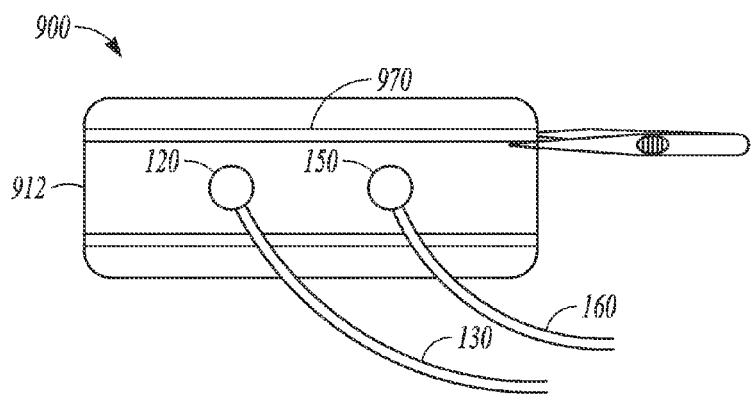
FIGS. 9A-C illustrate, by way of example, an embodiment of the adhesion patch with one or more wires that function as an adhesion assistive structure and a release mechanism.

FIG. 9A illustrates, by way of example, an embodiment of the adhesion patch 900 with an adhesion assistive structure and a release mechanism. The adhesion patch 900 is a specific embodiment of the adhesion patch 110. The adhesion patch 900 may include one or more wires 970 (two shown in FIGS. 9A-C) on the surface or within the adhesion patch 900. The wires 970 may function as a adhesion assistive structure that are configured for assisting the user to position the adhesion patch to the exterior of the blood vessel 780. The wires 970 may be made of shape-memory material. In one embodiment, the wires 970 are made out of nickel-titanium (NiTi) alloy that can maintain the adhesion patch 900 in a pre-determined shape. In another embodiment, the wires 970 are made of ductile stainless steel (SS) material that can be formed into a custom curvature or shape by the user. The wires 970 may also be made of materials including cobalt-chromium alloys, L-605, MP35N, and 316 LVM stainless steel. In some other embodiments, the wires are made of plastic or monofilament polyamide materials. In some embodiments, a plurality of wires are configured to form a mesh or lattice structure that functions as an adhesion assistive structure. Such structure may provide additional rigidity to the adhesion patch.

Figure 9B:
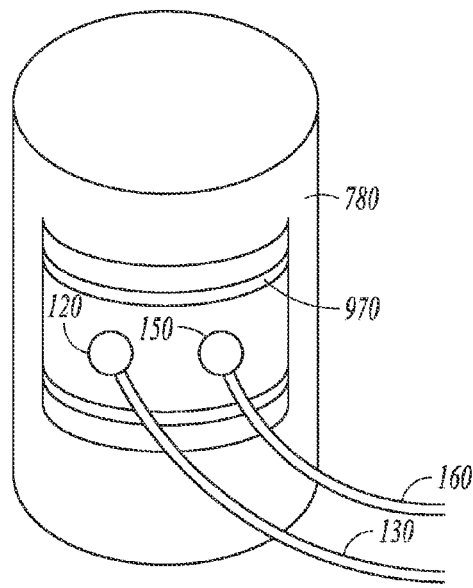

As illustrated in FIG. 9B, the wires 970 provide a rigid shape that would allow the adhesion patch 900 to wrap the adhesion patch 900 around the anatomical structure such as the exterior of the blood vessel 780, and keep the adhesion mechanisms (including the suction cups 610 and the air pressure channels 320) and the stimulation electrodes in contact for better adhesion. The wires 970 may be configured to desired shape, and cause the adhesion patch to maintain in the desired shape. In some embodiments, the wires 970 may be convexly shaped to make the adhesion patch 900 maintain conformity with the blood vessel 780. In some embodiments, the wires 970 may be formed into a cuff shape, promoting contact and adhesion of the adhesion patch to the anatomical surface of the target site.

Figure 9C:
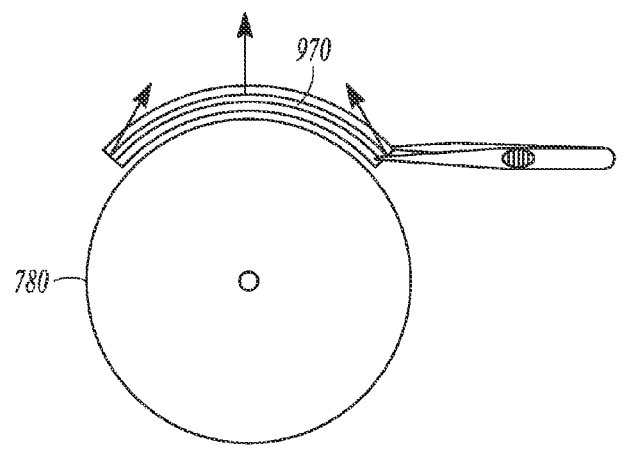

The wires 970 may not only function as shaping and adhesion assistive structure that makes the adhesion patch maintain conformity with the blood vessels, but may also be configured to function as a release mechanism that allows for use by the user to disengage the adhesion patch 900 from the exterior of the blood vessel 780. As illustrated in FIGS. 9A-B, the adhesion patch 900 has an edge 912, and the one or more wires 970 each includes at least one end extending to the edge 912 of the adhesion patch 900. As illustrated in FIG. 9C, the release mechanism may involve pulling on the midpoint of the wires 970 (shown by the arrow) using a surgical tool such as forceps, thereby releasing the adhesion surface row by row. Such a releasing mechanism may reduce the removal force if repositioning of the adhesion patch is desired. It also may help reduce the trauma associated with the releasing the adhesion patch from the target tissue. In some embodiments, the release mechanism involves pulling on at least one end of the wires 970 with the surgical tool (shown by the arrows in FIG. 9C), thereby disengaging the adhesion patch from the exterior of the blood vessel 780.

Although the wires 970 as illustrated in FIGS. 9A-C are configured to "across" the adhesion pad, the wires 970 may be incorporated into the adhesion patch in other orientation and manners. In some embodiments, the wires are along the edges of the adhesion path. The wires may form a loop, a semicircle, or an arc of a circle along the edges of the adhesion patch to facilitate releasing of the adhesion patch by the user.

In some embodiments, the wires used for the shaping and adhesion assistive structures and the wires for the releasing mechanism are separate wires with different constructions. For example, the wires for shaping and adhesion assistive structure are attached to one surface of, or embedded within, the adhesion patch 900, white the wires for releasing mechanism may be attached at the outer surface and along the edges of the adhesion patch. In some embodiments, the wires 970 may be used as sites for permanent suturing of the adhesion patch to the target site of the blood vessel or adjacent anatomy.

Figure 10:
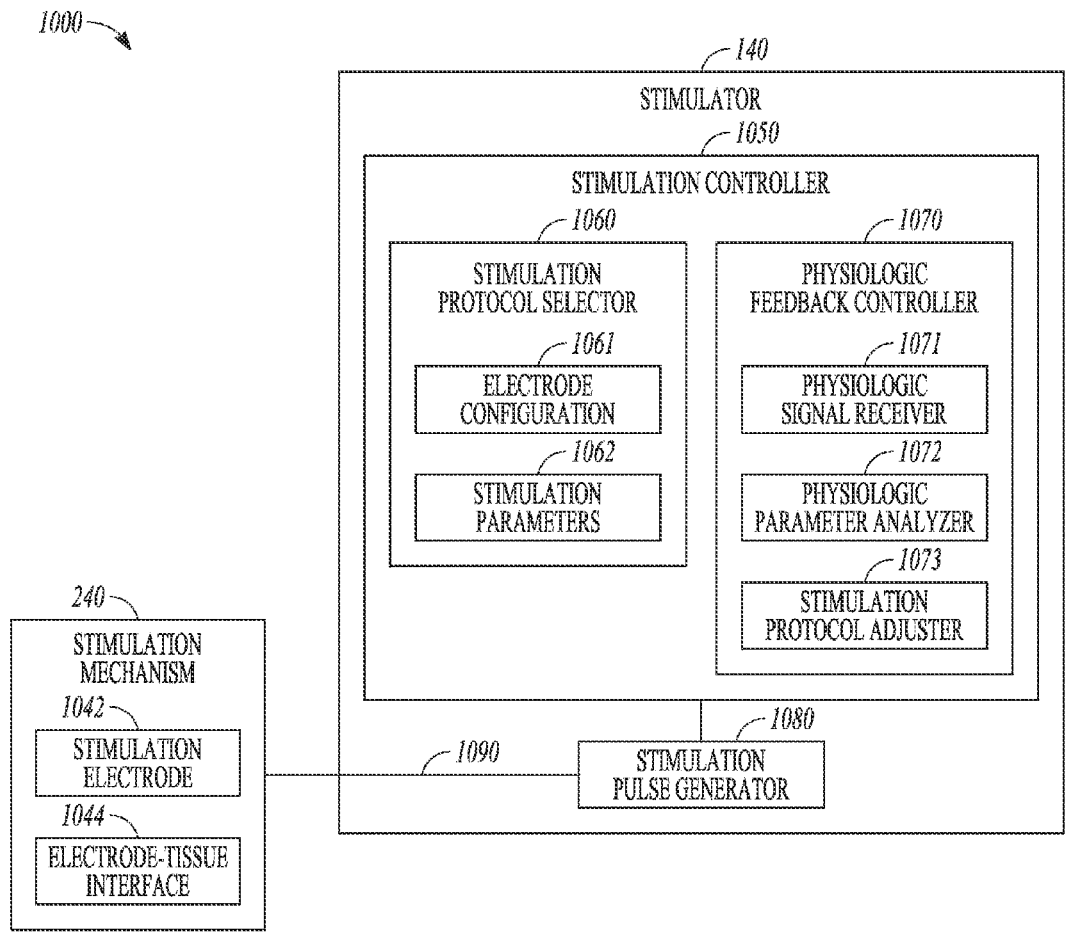
FIG. 10 illustrates, by way of example, an embodiment of a stimulation system.

FIG. 10 illustrates, by way of example, an embodiment of the stimulation system 1000 providing stimulations on the adhesion patch. The illustrated stimulation system 1000 includes a stimulation mechanism 240 and a stimulator 140. The stimulation mechanism 240 includes one or more stimulation electrodes 1042 and an electrode-tissue interface 1044. The one or more stimulation electrodes 1042 are configured to be in direct contact with the target tissue such as the exterior of the blood vessels, and deliver electrical energy to the target tissue to stimulate the target tissue. The electrode-tissue interface 1044 may be made of material with low contact impedance and atraumatic and biocompatible interaction with the target tissue. In some embodiments, the fluid or wet gel may be included on the electrode-tissue interface 1044 to reduce the tissue contact impedance, and thus to improve the efficiency of energy delivery to the target tissue.

The stimulator 140 generates electrical stimulation energy and controls the delivery of the stimulation energy to stimulation electrode 1042. The stimulator 140 may be external to the patient. In some embodiments, the stimulator may be an ambulatory stimulator including an implantable and a wearable stimulator. As illustrated in FIG. 10, the stimulator 140 includes a stimulation pulse generator 1080 and a stimulation controller 1050. The stimulation pulse generator 1080 is configured to generate the electrical pulses according to the commands from the stimulation controller 1050, and passes the electrical pulses to the stimulation electrodes 1042 via a channel 1090. In one embodiment, the channel 1090 may be a wire or a lead electrically coupled to the stimulation electrode 1042. In some embodiments, the channel 1090 may be a wireless channel coupled to the stimulation electrodes, where the wireless channel includes acoustic and radio frequency channels.

The stimulation controller 1050 includes a stimulation protocol selector 1060 and an optional physiologic feedback controller 1070. The stimulation protocol selector 1060 is configured to select from a plurality of stimulation protocols, or to program a stimulation protocol according to user's instructions. In some embodiments, the stimulation protocol selector 1060 is configured to allow the user to select electrode configuration 1061, such as selecting an anode and a cathode from a plurality of stimulation electrodes 1042 for bipolar stimulation of the target tissue. In other embodiments, the electrode configuration 1061 includes selecting an anode or a cathode from a plurality of stimulation electrodes 1042 for unipolar stimulation in reference to a reference electrode such as a can housing in an implantable stimulator. The stimulation protocol selector 1060 may also be configured to select or program a plurality of stimulation parameters 1062 for the stimulation pulse train. Examples of the stimulation parameters 1062 include stimulation amplitude (voltage or current), stimulation pulse frequency, pulse width, on and off-time of stimulation, duty cycle of the stimulation pulse train, and pulse waveform or morphology.

The physiologic feedback controller 1070 is configured to receive a physiologic response to the stimulation, and adjust the stimulation according to the physiologic response and one or more criteria associated with the physiologic response to stimulation. The physiologic feedback controller 1070 includes a physiologic signal receiver 1071, a physiologic parameter analyzer 1072, and a stimulation protocol adjuster 1073. The physiologic signal receiver 1071 is configured to receive a physiologic signal from a physiologic sensor. The physiologic signal may include blood pressure signal, electrocardiography signal, electrogram signal, respiration signal, and neural signal. Examples of physiologic sensor include an implantable or ambulatory sensor configured to sense the physiologic response, and an external invasive or noninvasive physiologic monitor configured to sense the physiologic response. The physiologic sensor may also include one or more modalities including impedance, acceleration, pressure, temperature, and other signals indicative of the changes in physiologic responses to the stimulation.

The physiologic parameter analyzer 1072 analyzes the received physiologic signal to determine the degree of change in a physiologic parameter due to the stimulation. For example, the physiologic parameter analyzer 1072 may be configured to analyze the blood pressure signal during the stimulation of the exterior of a carotid artery by computing a change in mean arterial pressure (MAP) during stimulation from the pre-stimulation MAP level.

Stimulation protocol adjuster 1073 is configured to adjust the stimulation parameters or electrode configuration if one or more pre-determined criteria are met. For example, if the MAP change is smaller than a pre-set threshold of MAP change, the stimulation protocol adjuster 1073 automatically increases the stimulation intensity by increasing the stimulation frequency, stimulation amplitude, pulse width, duty cycle, etc. in some embodiments, the stimulation protocol adjuster 1073 is configured to prompt the user to manually increase or decrease the stimulation intensity.

Figure 11:
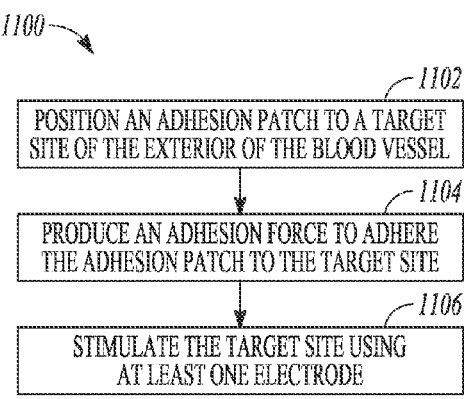
FIG. 11 illustrates, by way of example, an embodiment of a method for stimulating a target site of an exterior of a blood vessel.

FIG. 11 illustrates, by way of example, an embodiment of a method 1100 of stimulating a target site of an exterior of a blood vessel. The method 1100 may be used with the adhesion patch 110 to stimulate an exterior of a blood vessel or other tissues or organs. The method 1100 starts at 1102 with positioning an adhesion patch to a target site of the exterior of the blood vessel. The adhesion patch may include one or more electrodes electrically coupled to a stimulator, such as the stimulator 140 as illustrated in FIGS. 4-6 and 10. In some embodiments, the adhesion patch includes an active adhesion mechanism, as illustrated by adhesion patch 110 in FIG. 2.

At 1104, an adhesive force is produced to adhere the adhesion patch to the target site of the exterior of the blood vessel. The adhesive force is sufficiently strong to adhere the adhesion patch to the target site of the exterior of the blood vessel, and to operationally position at least one electrode to the target site. The adhesive force may be generated through an active adhesion mechanism. In some embodiments, the active adhesion mechanism includes evacuating air from between the adhesion patch and the exterior of the blood vessel to adhere the patch to the exterior of the blood vessel.

Once an adhesion patch is adhered to the target site, at 1106, the target site is stimulated using at least one electrode that is provided on the adhesion patch. In one embodiment, the stimulation pulses are delivered according to a pre-determined protocol that defines the stimulation intensity and stimulation time. In some embodiment where more than one electrode is provided, the stimulation is delivered according to a pre-determined electrode configuration that defines the anode and cathode electrodes used for stimulation. In some embodiments, the stimulation may be adjusted automatically or manually according to physiologic response to the stimulation. For example, if the physiological response does not meet one or more criteria, the stimulation protocol, including the stimulation electrode configuration and the stimulation protocol, may be adjusted; and new stimulation pulses can be delivered to the target site via the electrodes on the adhesion patch.

Figure 12:
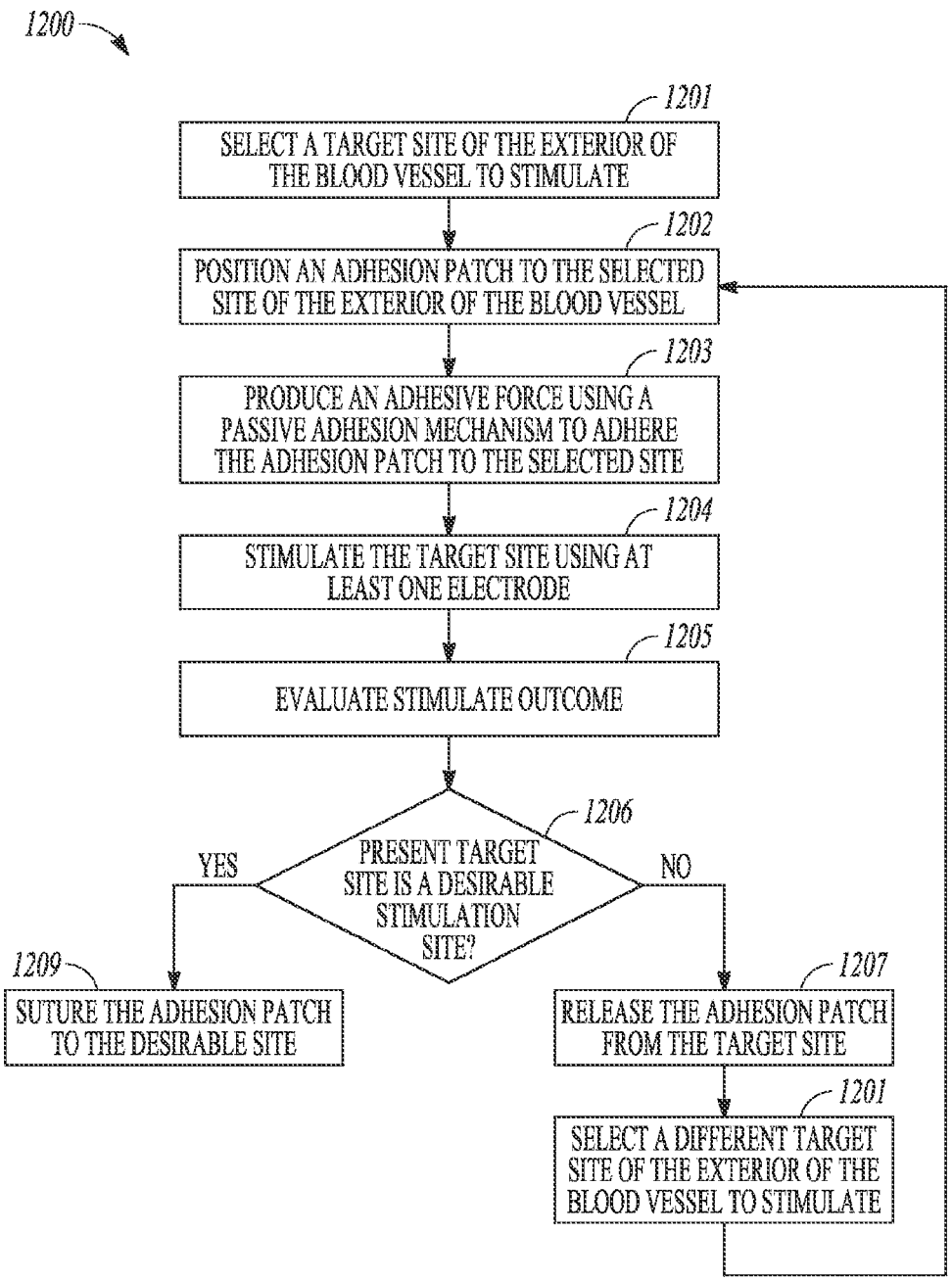
FIG. 12 illustrates, by way of example, an embodiment of a method for selecting a desirable stimulation site on the exterior of a blood vessel.

FIG. 12 illustrates, by way of example, an embodiment of a method 1200 for selecting a desirable stimulation site on the exterior of a blood vessel. At 1201 an initial site on the exterior of the blood vessel is selected for stimulation. At 1202, an adhesion patch is positioned at the selected site. The adhesion patch, such as the adhesion patch 110, may include an adhesion mechanism, a releasing mechanism, and a stimulation mechanism. To allow the adhesion patch to be securely and atraumatically attached to the target site on the exterior of the blood vessel, the side on the adhesion patch with adhesion mechanism may be positioned to the target stimulation site. At 1203, an active adhesive force is produced to allow the adhesion patch to be adhered to the target site. The adhesive force is sufficiently strong to allow the adhesion patch to be securely adhered to the target site; and the one or more electrodes to be in close contact with the target tissue. In some embodiments, the active adhesion mechanism may include one or more air channels in the adhesion patch, as illustrated in FIGS. 4-5. The one or more air channels pass the negative air pressure generated by an air pressure source to the patch-tissue interface, evacuating the air from between the adhesion patch and the exterior of the blood vessel, and causing the adhesion patch to adhere to the exterior of the blood vessel. In some embodiments, the active adhesion mechanism may include one or more suction cups connected with one or more air channels in the adhesion patch, as illustrated in FIG. 6. The negative air pressure produced by the air pressure source may be passed to the suction cups and causes the suction cups and hence the adhesion patch to adhere to the exterior of the blood vessel.

At 1204, the target site is stimulated using at least one electrode that is provided on the adhesion patch. The response to the stimulation is recorded and evaluated at 1205. In one embodiment, the evaluation was performed by sensing one or more physiologic signals, analyzing a physiologic parameter computed from the sensed physiologic signal, and determining the significance of the physiologic response to the delivered stimulation by, for example, comparing the physiologic parameter to a pre-determined threshold. If the responses to stimulation at other sites are available, at 1206, the responses of different stimulation sites are compared to determine if the present stimulation site is "desirable". In some embodiments, among of the stimulation sites on the exterior of a blood vessel, a desirable site is determined to be the tested that, when stimulated, results in the greatest drop in mean arterial pressure from a pre-stimulation baseline level. In some other embodiments, a desirable site is determined to be the tested site that, when stimulated, results in the lowest mean arterial pressure.

If at 1206 the present stimulation site is deemed "desirable", then at 1209 the site selection process is completed, and the adhesion patch can be sutured at the desirable site, or secured at the desirable site with tissue growth, for chronic electrical stimulation. However, if the present site is not deemed desirable, then at 1207, the adhesion patch is disengaged from the present stimulation site. The disengagement of the adhesion patch may be achieved by using the release mechanism on the adhesion patch. The release mechanism may include producing positive air pressure in between the adhesion patch and the exterior of the blood vessel to disengage the adhesion patch from the exterior of the blood vessel. The positive air pressure may be generated by the air pressure source and passed on to the patch-tissue interface through the air pressure channels on the adhesion patch, as illustrated in FIGS. 4-6. In some embodiments, the active release mechanism using the positive air pressure may be used together with one or more passive release mechanisms including a release tab 770 along at least a portion of the peripheral margin 712 as illustrated in FIG. 7, a portion of the non-adhesive boundary region 870 on the adhesion patch as illustrated in FIG. 8, and one or more wires 970 each of which including at least one end extending to an edge of the adhesion patch, as illustrated in FIG. 9. These passive release mechanisms allow for use by the user to peel off the adhesion patch from the exterior of the blood vessel with no or minimal trauma to the tissue. At 1208, a different target site can be selected front the exterior of the blood vessel, and the released adhesion patch can be re-positioned to the new site and the stimulation can be repeated at the new site.

Figure 13:
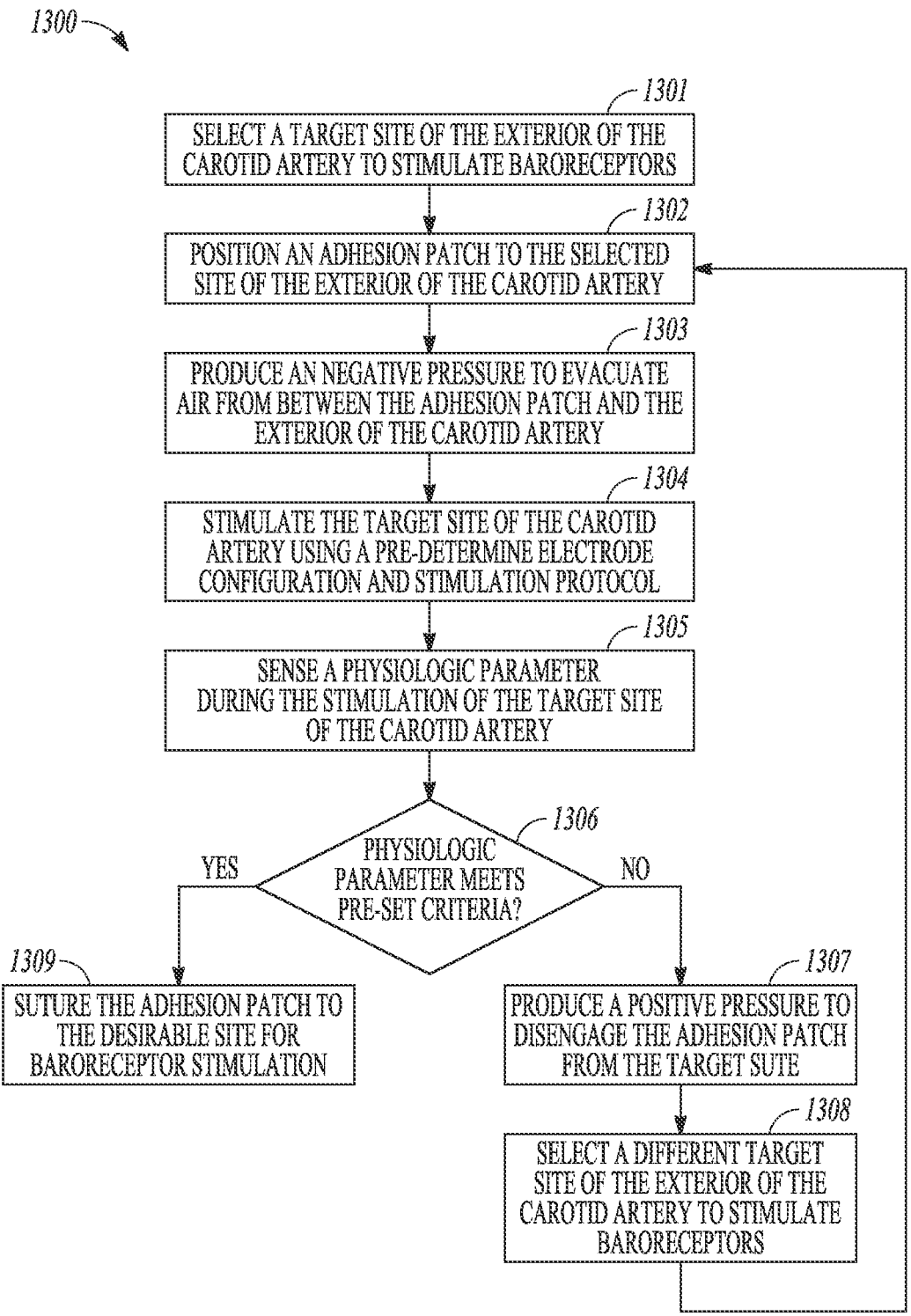
FIG. 13 illustrates, by way of example, an embodiment of a method for selecting a desirable site of an exterior of a carotid artery for baroreceptor stimulation.

FIG. 13 illustrates, by way of example, an embodiment of a method 1300 to select a desirable site of an exterior of a carotid artery for baroreceptor stimulation. This method can be used, for example, in the process of baromodulation mapping before implant of a baromodulation device for chronic blood pressure control. By extensive and effective mapping of the internal carotid arteries, a desirable stimulation location on the carotid artery can be found which provides safe and most efficacious baroreceptor stimulation for blood pressure control.

At 1301 an initial site on the exterior of the carotid artery for stimulation is selected. Then, at 1302, an adhesion patch is positioned at the selected site on the exterior of the carotid artery. At 1303, an adhesive force is produced to allow the adhesion patch to be adhered to the target site. The produced adhesive force is sufficiently strong to allow the adhesion patch to be securely adhered to the target site; and the one or more electrodes to be in close contact with the target tissue. As The adhesive force may be produced using a negative pressure to evacuate the air from between the adhesion patch and the exterior of the carotid artery, thereby causing the adhesion patch to adhere to the exterior of the carotid artery. At 1304, the target site is stimulated using at least one electrode that is provided on the adhesion patch. In some embodiments, the stimulation delivered at one target site includes a plurality of stimulation vectors and electrode configurations, a plurality of stimulation protocols with different stimulation parameters (e.g., stimulation intensity, frequency, pulse width, etc.), and a permutation of the stimulation electrode configurations and stimulation protocols. On the first target site of the carotid artery, stimulation pulses according to the selected stimulation protocol and electrode configuration are delivered, and a physiologic parameter during the stimulation is sensed at 1305. The physiologic parameter may include blood pressure signal, electrocardiography signal, electrogram signal, respiration signal, and neural signal. The physiologic parameter may be sensed using an implantable or ambulatory sensor, or an external invasive or noninvasive physiologic monitor that senses the physiologic response. In various embodiments, the sensor may include one or more modalities including impedance, accelerometer, chemical, pressure, and other signals indicative of the changes in physiologic responses to the stimulation. The physiologic parameter is analyzed to determine the degree of change in the physiologic parameter due to the stimulation. In one embodiment, during each stimulation electrode configuration and stimulation protocol, blood pressure signal during the stimulation of the exterior of a carotid artery is sensed, and the change in mean arterial pressure (MAP) from the pre-stimulation MAP level is determined. The physiologic response is compared to a pre-set criterion at 1306 to determine if the present site of stimulation is the desirable site. In one embodiment, the pre-set criterion includes a threshold value of the change of the MAP during stimulation from a pre-stimulation baseline MAP level. In another embodiment, the pre-set criterion includes a threshold value of the MAP level during stimulation.

If at 1306 the present stimulation site was deemed desirable, then at 1309, the site selection is completed, and the adhesion patch can be sutured, or secured with tissue growth, at the desirable site of the carotid artery for chronic or permanent programmed stimulation when necessary. However, if the physiologic parameter does not meet the pre-set criterion (e.g., the drop in MAP during stimulation at the present site is smaller than a pre-set threshold level for the change in MAP, or the absolute MAP during stimulation is higher than a pre-set MAP level), then at 1307, the adhesion patch is disengaged from the present stimulation site. The disengagement of the adhesion patch can be achieved using the release mechanism on the adhesion patch. In one embodiment, the release mechanism may include producing positive air pressure in between the adhesion patch and the exterior of the carotid artery to disengage the adhesion patch from the exterior of the carotid artery. In other embodiments, the active release mechanism using the positive air pressure can be used together with one or more passive release mechanisms including a release tab 770 along at least a portion of the peripheral margin 712 as illustrated in FIG. 7, a portion of the non-adhesive boundary region 870 on the adhesion patch as illustrated in FIG. 8, and one or more wires 970 each of which including at least one end extending to an edge of the adhesion patch, as illustrated in FIG. 9. Then, at 1308, a different target site may be selected from the exterior of the carotid artery. The released adhesion patch can be re-positioned to the new site, and the stimulation can be repeated on the new site.

The above detailed description is intended to be illustrative, and not restrictive. Other embodiments will be apparent to those of ordinary skills in the art upon reading and understanding the above description. The scope of the disclosure should, therefore, be determined with references to the appended claims, along with the full scope of equivalents to which such claims are entitled.

What is claimed is:

1. A system, comprising
   at least one electrode;
   an adhesion patch, wherein the adhesion patch includes an active adhesion mechanism configured to produce a negative air pressure sufficient to adhere the adhesion patch to an exterior of a blood vessel and to operationally position the at least one electrode for use in electrically stimulating a target site of the blood vessel; and
   a stimulator configured to generate electrical stimulation pulses, wherein the stimulator is operationally connected to the at least one electrode to stimulate the target site of the blood vessel;
   wherein the at least one electrode includes an electrode pattern of more than one electrode, and the system is configured to selectively deliver electrical stimulation pulses using different electrodes selected from within the electrode pattern.

2. The system of claim 1, wherein the adhesion patch includes an air pressure port coupled to the active adhesion mechanism, the air pressure port configured to receive desired air pressure to control adhesion to the blood vessel.

3. The system of claim 2, further comprising an air pressure controller, wherein the air pressure controller is coupled to an air pressure generator and configured to produce the desired air pressure and feed the desired air pressure to the air pressure port.

4. The system of claim 2, wherein the active adhesion mechanism includes one or more air channels configured to pass the desired air pressure to between the adhesion patch and the exterior of the blood vessel.

5. The system of claim 4, wherein the one or more air channels are configured to pass negative air pressure to evacuate air from between the adhesion patch and the exterior of the blood vessel to adhere the patch to the exterior of the blood vessel.

6. The system of claim 5, wherein the adhesion patch includes one or more suction cups, the one or more suction cups configured to open to the one or more air channels and receive the negative air pressure through the one or more air channels to evacuate air from between the one or more suction cups and the exterior of the blood vessel.

7. The system of claim 2, wherein the adhesion patch includes a release mechanism configured for use to disengage the adhesion patch from the exterior of the blood vessel.

8. The system of claim 7, wherein the release mechanism includes one or more air channels configured to pass positive air pressure to between the adhesion patch and the exterior of the blood vessel to disengage the adhesion patch from the exterior of the blood vessel.

9. A system, comprising
at least one electrode; and
an adhesion patch, wherein the adhesion patch includes:
an active adhesion mechanism, configured to produce a negative air pressure sufficient to adhere the adhesion patch to an exterior of a blood vessel and to operationally position the at least one electrode for use in electrically stimulating a target site of the blood vessel; and
a suture area configured for use by the user to suture the adhesion patch in position on the exterior of the blood vessel.

10. A system, comprising:
at least one electrode; and
an adhesion patch, wherein the adhesion patch includes an active adhesion mechanism configured to produce a negative air pressure sufficient to adhere the adhesion patch to an exterior of a blood vessel and to operationally position the at least one electrode for use in electrically stimulating a target site of the blood vessel;
wherein the adhesion patch is configured with a size and a shape to partially wrap around the blood vessel and be in conformity with the blood vessel.

11. A method of stimulating a target site of an exterior of a blood vessel, the method comprising:
adhering an adhesion patch to the target site of the exterior of the blood vessel, wherein adhering the adhesion patch includes producing an adhesive force using an active adhesion mechanism on the adhesion patch to cause the adhesion patch to adhere to the target site and to operationally position at least one electrode to the target site; and
stimulating the target site using the at least one electrode, including stimulating the target site using a plurality of stimulation vectors with different combinations of electrodes including the at least one electrode.

12. The method of claim 11, wherein adhering the adhesion patch includes evacuating air from between the adhesion patch and the exterior of the blood vessel to adhere the patch to the exterior of the blood vessel.

13. The method of claim 11, further comprising releasing the adhesion patch from the blood vessel without significant trauma to the blood vessel, wherein releasing the adhesion patch includes producing positive air pressure in between the adhesion patch and the exterior of the blood vessel to disengage the adhesion patch from the exterior of the blood vessel.

14. The method of claim 13, further comprising re-adhering the adhesion patch to a different target site of the blood vessel, and stimulating the different target site of the blood vessel using the at least one electrode.

15. The method of claim 11, further comprising suturing the adhesion patch to chronically hold the adhesion patch at the desirable stimulation site.

16. The method of claim 11, wherein adhering the adhesion patch includes partially wrapping the patch around the blood vessel.

17. A method of determining a desirable site of an exterior of a carotid artery for baroreceptor stimulation, the method comprising:
adhering an adhesion patch to a first site of the exterior of the carotid artery, wherein adhering the adhesion patch includes producing an adhesive force using an active adhesion mechanism on the adhesion patch to cause the adhesion patch to adhere to the first site and to operationally position at least one electrode to the first site;
stimulating the first site using the at least one electrode, including stimulating the first site using a plurality of stimulation vectors with different combinations of electrodes including the at least one electrode;
sensing a physiological parameter during the stimulation of the first site;
disengaging the adhesion patch from the first site using a release mechanism on the adhesion patch and re-adhering the adhesion patch to a second site of the exterior of the carotid artery; and
determining a desirable stimulation site, wherein determining the desirable stimulation site includes comparing the sensed physiological parameter during stimulation at the first site and the sensed physiological parameter during stimulation at the second site.

18. The method of claim 17, wherein:
producing the adhesive force using the active adhesion mechanism on the adhesion patch includes evacuating air from between the adhesion patch and the exterior of the carotid artery to adhere the patch to the exterior of the carotid artery; and
disengaging the adhesion patch includes receiving positive air pressure and passing the positive air pressure to between the adhesion patch and the exterior of the carotid artery to disengage the adhesion patch from the exterior of the carotid artery.

19. The method of claim 17, wherein adhering the adhesion patch includes partially wrapping the patch around the blood vessel.

20. A method of stimulating an exterior of a carotid artery, the method comprising:
adhering an adhesion patch to a first site of the exterior of the carotid artery, wherein adhering the adhesion patch includes producing an adhesive force using an active adhesion mechanism on the adhesion patch to cause the adhesion patch to adhere to the first site and to operationally position at least one electrode to the first site;
stimulating the first site using the at least one electrode;
sensing a physiological parameter during the stimulation of the first site;
disengaging the adhesion patch from the first site using a release mechanism on the adhesion patch and re-adhering the adhesion patch to a second site of the exterior of the carotid artery;
determining a desirable stimulation site, wherein determining the desirable stimulation site includes comparing the sensed physiological parameter during stimulation at the first site and the sensed physiological parameter during stimulation at the second site; and
suturing the adhesion patch to chronically hold the adhesion patch at the desirable stimulation site.

* * * * *